US00PP11944P2

(12) United States Plant Patent
Meerow

(10) Patent No.: US PP11,944 P2
(45) Date of Patent: Jun. 19, 2001

(54) ALSTROEMERIA PLANT NAMED 'LAS OLAS'

(75) Inventor: Alan Meerow, Davie, FL (US)

(73) Assignee: Florida Foundation Seed Producers, Greenwood, FL (US)

( * ) Notice: Subject to any disclaimer, the term of this patent is extended or adjusted under 35 U.S.C. 154(b) by 0 days.

(21) Appl. No.: 09/263,506

(22) Filed: Mar. 3, 1999

(51) Int. Cl.[7] ..... A01H 5/00

(52) U.S. Cl. ..... Plt./309

(58) Field of Search ..... Plt./309

(56) References Cited

PUBLICATIONS

UPOV–ROM GTIM Computer Database 1999/02, GTI Jouve Retrieval Software, citation for 'Las Olas', May 1999.*

* cited by examiner

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Alstroemeria plant named 'Las Olas', characterized by its vigorous, semi-dwarf plant habit; erect peduncles; umbellate cymes with numerous pink and white-colored flowers; excellent cut flower yield; consistent flowering from April to July in south Florida; and exceptional high temperature, high humidity and rain tolerance.

1 Drawing Sheet

BACKGROUND OF THE INVENTION

The present invention relates to a new and distinct cultivar of Alstroemeria plant, botanically known as *Alstroemeria pulchella*×*A. pelegrina*, and hereinafter referred to by the cultivar name 'Las Olas'.

The new Alstroemeria is a selection by the Inventor in Fort Lauderdale, Fla., from open-pollinated seed informally known as "Meyer's Hybrid" strain. The original hybrids between *Alstroemeria pelegrina* L. (Chilean origin) and *Alstroemeria pulchella* L. f. (Brazilian origin) were made by Mr. Fred Meyer, of Bonsall, Calif., in the early 1980's by embryo rescue and subsequent tetraploidization with colchicine.

The Inventor received seed from Mr. Meyer in 1991 and 'Las Olas' was selected from several hundred plants grown outdoors in a controlled environment in Fort Lauderdale, Fla., on the basis of its cut flower potential and exceptional high temperature, high humidity and rain tolerance.

Since 1992, asexual reproduction of the new cultivar by divisions in Fort Lauderdale, Fla., has shown that the unique features of this new Alstroemeria are stable and reproduced true to type in successive generations.

BRIEF SUMMARY OF THE INVENTION

The following traits have been repeatedly observed and are determined to be the unique characteristics of 'Las Olas'. These characteristics in combination distinguish 'Las Olas' as a new and distinct Alstroemeria:

1. Vigorous, semi-dwarf perennial plants with erect peduncles which support umbels of pink and white-colored flowers.

2. Freely flowering habit; typically about 140 flowers per plant.

3. Excellent cut flower yield, usually about 43 flowering stems per meter per year.

4. Consistent flowering from April to July in south Florida.

5. Exceptional warm weather, high humidity and rain tolerance.

Compared to plants of *Alstroemeria pulchella*, plants of the new Alstroemeria differ in the following characteristics:

1. Plants of the new Alstroemeria have smaller leaves than plants of *Alstroemeria pulchella*. In addition leaves of the new Alstroemeria are evenly distributed along the stems whereas leaves of *Alstroemeria pulchella* are mostly clustered towards the apices.

2. Flowers of the new Alstroemeria are more open and wider than flowers of *Alstroemeria pulchella* which are more tubular and narrower.

3. Plants of the new Alstroemeria flower in south Florida from April to July whereas plants of *Alstroe5meria pulchella* flower from January to April.

4. Flowers of the new Alstroemeria are purple and white in color whereas flowers of *Alstroemeria pulchella* are red and green in color.

Compared to plants of *Alstroemeria pelegrina*, plants of the new Alstroemeria differ in the following characteristics:

1. Plants of the new Alstroemeria are taller than plants of *Alstroemeria pelegrina*.

2. Flower parts of the new Alstroemeria are slightly narrower than flower parts of *Alstroemeria pelegrina*.

3. Plants of the new Alstroemeria have more flowers per stem than plants of *Alstroemeria pelegrina*.

4. Flowers of the new Alstroemeria do not have a yellow spot on the inner tepals that is evident on flowers of *Alstroemeria pelegrina*.

The new Alstroemeria can be compared to the commercial Alstroemeria cultivar 'Toluca' (not patented), however, in side-by side comparisons conducted in Fort Lauderdale, Fla., plants of the new Alstroemeria were much shorter and much more high temperature-tolerant than plants of the cultivar 'Toluca'.

BRIEF DESCRIPTION OF THE PHOTOGRPAH

The accompanying colored photograph illustrates the overall appearance of the new Alstroemeria, showing the colors as true as it is reasonably possible to obtain in colored reproductions of this type. Colors in the photographs may differ slightly from the color values cited in the detailed botanical description which more accurately describe the actual colors of the new Alstroemeria. The photograph comprises a side perspective view of typical flowers and leaves of the new Alstroemeria.

DETAILED BOTANICAL DESCRIPTION

Plants of the new Alstroemeria have not been observed under all possible environmental conditions. The phenotype may vary significantly with variations in environment such as fertilizer rate, water status, temperature and light level, without, however, any variance in genotype.

The following observations, measurements and values describe flowering plants grown outdoors in ground beds in Fort Lauderdale, Fla., under conditions which closely approximate commercial cut flower production. Plants were covered with polypropylene shadecloth that provided about a 50 percent reduction in light level.

In the following description, color references are made to The Royal Horticultural Society Colour Chart except where general terms of ordinary dictionary significance are used.

Botanical classification: *Alstroemeria pulchella*×*A. pelegrina* cultivar 'Las Olas'.

Parentage: Selection from open-pollinated seed of "Meyer's Hybrid" strain, *Alstroemeria pulchella*×*pelegrina*.

Propagation:

*Method.*—By divisions.

*Time to initiate roots.*—Summer: About 10 days at 30° C. Winter: About 15 days at 25° C.

*Time to develop roots.*—Summer: About 30 days at 30° C. Winter: About 45 to 60 days at 20° C.

*Rooting habit.*—Fibrous and also fleshy; root tubers form at apices.

Plant description:

*Form.*—Semi-dwarf; upright, oval-shaped, rhizomatous perennial flowering plant; numerous erect peduncles support umbels of pink-colored flowers.

*Branching habit.*—Freely basal branching; about 30 to 50 lateral branches per plant.

*Crop time.*—About 6 to 8 months are required to produce a flowering plant.

*Cut flower yield.*—Very productive; about 43 flowering stems per square meter per year are produced.

*Usage.*—Excellent garden and cut flower performance. May also be grown as a container plant.

*Growth rate.*—Rapid and vigorous.

*Plant height.*—About 39 to 65 cm.

*Plant diameter.*—About 50 to 75 cm.

*Vegetative stems.*—Length: About 39 to 57 cm. Diameter: About 4 mm. Internode length: About 2 to 3 cm. Texture: Glabrous. Stem color: Green, 135D.

*Foliage description.*—Leaves simple, alternate, generally symmetrical and abundant. Quantity per lateral branch: About 12 to 20. Length: About 5 to 10 cm. Width: About 1.5 to 2 cm. Shape: Oblanceolate; apex, acute; base, attenuate. Margin: Entire. Texture: Glabrous. Color: Young and mature leaves, upper surface: 135C. Young and mature leaves, lower surface: 136C. Venation, upper surface: 135C. Venation, lower surface: 136C.

Flower description:

*Flower type and habit.*—Numerous zygomorphic, "butterfly-type", funnel-form to campanulate; flowers arranged in umbellate cymes. Flowers self-cleaning.

*Floriferousness.*—Freely flowering; typically one to four flowers per cyme, three to five cymes per umbel, three to 17 flowers per lateral stem, and about 140 flowers per plant.

*Flowering season.*—Consistent flowering from April to July in south Florida. Plants start flowering about six months after planting.

*Flower buds just showing color.*—Length: About 1.5 cm. Diameter: About 1 cm. Shape: Cylindrical. Color: 73B to 74C. Rate of opening: About one per day.

*Flower longevity on the plant.*—About five days.

*Cut flower longevity.*—About two weeks.

*Fragrance.*—None.

*Flower length.*—About 6 to 7 cm.

*Flower width, laterally.*—About 5.8 to 6.3 cm.

*Flower depth, dorsal-ventrally.*—About 4.5 to 5.8 cm.

*Perianth.*—Arrangement: Two separate whorls of three tepals each. Length: Outer tepals, about 5 to 5.6 cm; inner tepals, about 5.5 to 5.9 cm. Width: Outer tepals, about 2 to 2.2 cm; inner tepals, about 1.2 to 1.5 cm. Shape: Outer tepals, ovate with emarginate apex; inner tepals, elliptic with acuminate apex. Margin: Towards base, entire; towards apex, finely serrate. Texture: Smooth. Color: Outer tepals, upper surface: 74D; 64A towards center of tepal; green, 141B, at apex. Outer tepals, lower surface: 74D; 64A towards center of tepal; green, 141B, at apex. Inner tepals, upper surface: White with elongated reddish purple, 59A, spots/streaks; apicula, green close to 136C. Inner tepals, lower surface: 74D with a central white zone; reddish purple, 59A, spots/streaks, fainter than upper surface; apicula, green.

*Peduncles.*—Length: About 55 to 65 cm. Strength: Moderately strong. Peduncle aspect: Upright. Color: 135D.

*Reproductive organs.*—Androecium: Stamen number: Typically six. Filament length: About 2 cm. Anther length: About 2 mm. Anther shape: Elliptical. Anther color: 74D. Pollen amount: Moderate. Pollen color: White. Gynoecium: Pistil length: About 8 cm. Style length: About 7.5 cm. Style color: 74D. Stigma shape: Trifid. Stigma color: 74D. Ovary color: 135C.

Seed development: Seed development has not been observed.

Disease resistance: Resistance to pathogens common to Alstroemeria has not been observed.

Weather tolerance: Exceptional warm weather, high humidity and rain tolerance. Plants are able to withstand high day and night temperatures, high humidity levels, and periodic torrential rains associated with subtropical and warm temperate climates.

It is claimed:

1. A new and distinct Alstroemeria plant named 'Las Olas', as illustrated and described.

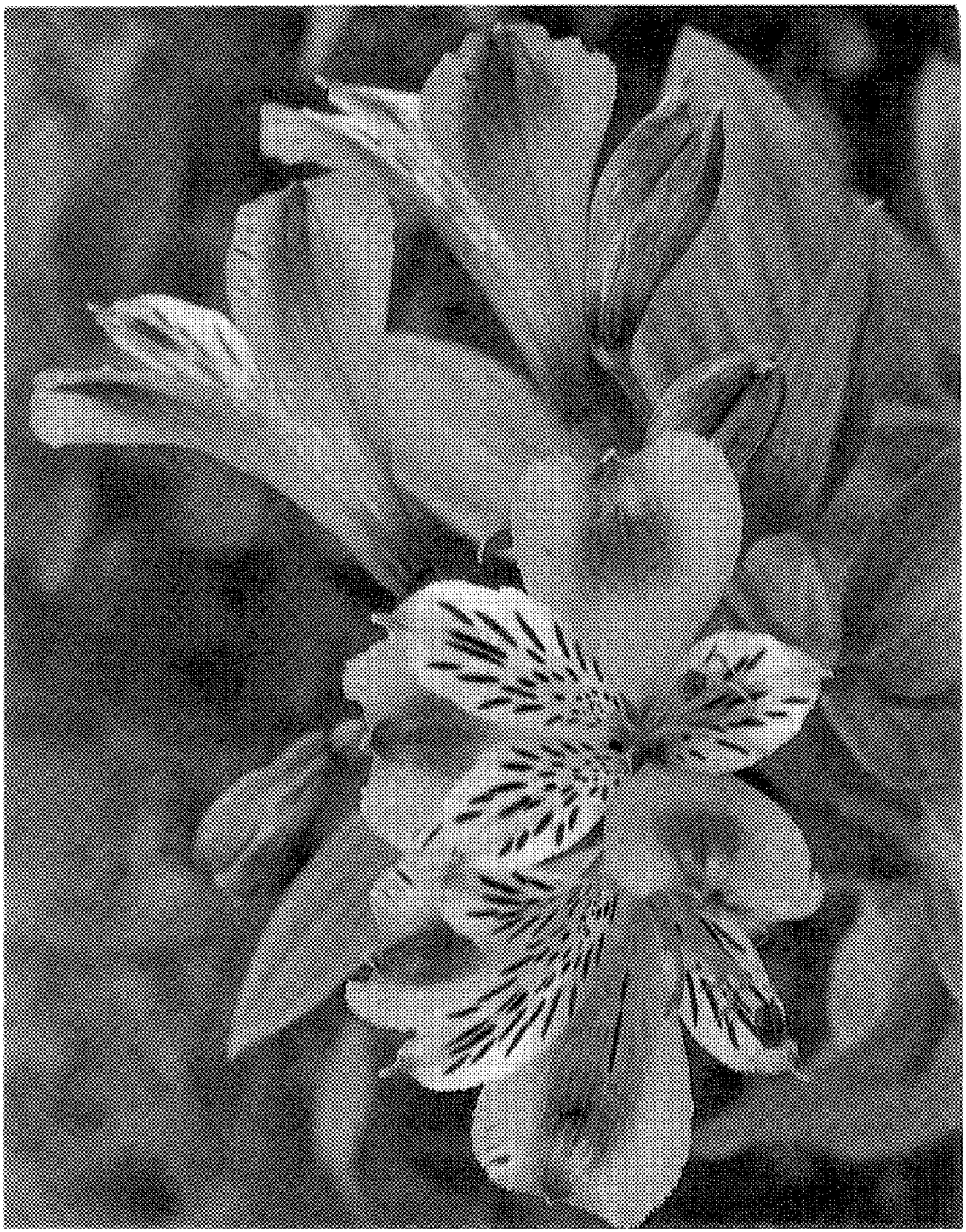

* * * * *